United States Patent [19]

Williams

[11] 4,043,343
[45] Aug. 23, 1977

[54] FORCEPS

[76] Inventor: Robert W. Williams, 3201 S. Maryland Parkway, Las Vegas, Nev. 89109

[21] Appl. No.: 601,060

[22] Filed: Aug. 1, 1975

[51] Int. Cl.$^2$ .................... A61B 17/28; A61B 17/32
[52] U.S. Cl. .................................. 128/321; 128/305
[58] Field of Search ........................................ 128/321

[56] References Cited

U.S. PATENT DOCUMENTS

| 984,756 | 2/1911 | Frisch | 128/321 |
|---|---|---|---|
| 2,751,908 | 6/1956 | Wallace | 128/321 |
| 2,790,437 | 4/1957 | Moore | 128/321 X |
| 2,854,005 | 9/1958 | Vido | 128/321 |

FOREIGN PATENT DOCUMENTS 287,323   3/1953   Switzerland .......................... 128/321

Primary Examiner—Channing L. Pace
Attorney, Agent, or Firm—Jerry R. Seiler

[57] ABSTRACT

In forceps having a pair of handles one of which is hinged for reciprocal movement relative to the other, extension arms between the handles one of the arms being reciprocally slidable along the other arm, upper and lower jaw members one of which is hinged for reciprocal movement relative to the other which reciprocal movement of the jaws and arms is in response to reciprocal handle movement, and the slidable arm may be disengaged for cleaning, the improvement comprises a locking member pivotally mounted for engaging one side of the slidable arm in the locked position.

3 Claims, 6 Drawing Figures

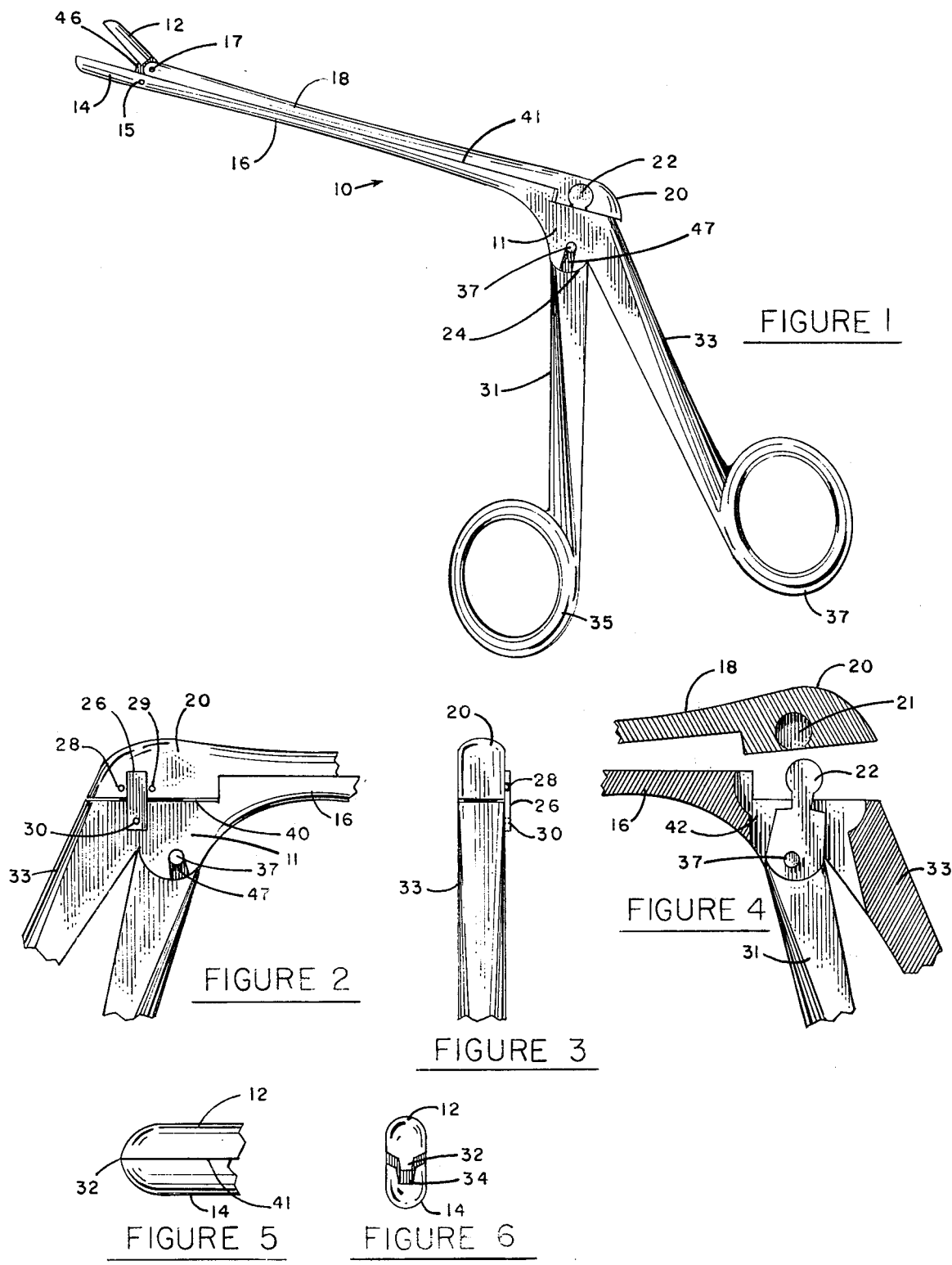

FORCEPS

BACKGROUND OF THE INVENTION

Forceps are designed to be used in surgical procedures for cutting and removing tissue and other anatomical portions. Of particularly advantageous design are forceps having a pair of reciprocal jaws at one end opposite reciprocal handles, such device being especially suitable for microlumbar discectomy procedures in which portions of a patient's intervertebral disc material is to be removed. Normally, the reciprocal type forceps utilize a slidable arm connecting a reciprocal handle with a reciprocal jaw and which arm is disengagable for the purpose of cleaning the instrument of organic matter that becomes lodged along the part line between the slidable arms. Although such a cleaning feature is highly advantageous, it has been found that when used in lumbar discectomy procedures, the surgeon often twists the instrument in order to remove disc material, and other cartilaginous, tendinous, or calcereous fibrous matter to such an extent that the slidable arm is disengaged thereby temporarily disrupting the use of the device until the arms are again connected. Obviously such interruption during the procedure is undesirable and it is to the obviation of such a problem that the present invention is intended and directed.

SUMMARY OF THE INVENTION

The forceps of the present invention are directed to those of the reciprocating handle, arm and jaw type, which operate in a scissor like manner, incorporating means for preventing accidental disengagement of the arms. The means comprises a member, hinged or pivoted for selected locking engagement against one side of a reciprocal arm.

For specific use in a micro-lumbar discectomy procedure, the forceps have the handles extending angularly relative to the arm and jaws whereby the surgeon may operate the jaws reciprocally with his dominant hand off to the side of the incision and so as to not interfere with the microscopic field of vision. The long thin arms extend into the incision as do the jaws at the ends of the arms, opposite the handles. In another embodiment, the jaws are designed so that one of them has a tooth with a cutting edge thereon while the other jaw has a slot of a shape for matingly receiving the tooth as well as a cutting surface thereon. Because of the tooth and slot, there is an uneven or somewhat irregular surface for better gripping the material for removal from the surgical area. These as well as other advantages will be evident from the following detailed description.

BRIEF DESCRIPTION OF THE DRAWINGS

FIG. 1 is a side view of the forceps of the invention;

FIG. 2 is an enlarged view of a portion of the opposite side of the forceps of FIG. 1 illustrating the locking member of the invention;

FIG. 3 is an end view of the arms thereof;

FIG. 4 is a side view, partially in section of a portion of the forceps of FIG. 1 showing disassembly of the arms;

FIG. 5 is a side view of another embodiment showing a portion of the jaws; and

FIG. 6 is a front view of the jaws of FIG. 5 partially opened.

DETAILED DESCRIPTION OF THE INVENTION

Referring initially to FIG. 1, there is shown a view of one side of the forceps 10 of the invention. The device comprises a pair of handles 31 and 33 terminating at one end in ring members 35 and 37 by which the surgeon may operate the instrument similar to a scissors by placing a finger and a thumb in the rings. In the device shown, handle 33 is stationary arm 16 and a stationary jaw 14, also integral with arm 16 opposite handle 33.

Arm 31 is movably secured on pivot pin 37 which extends through bridge portion 11 of handle 33. Moreover, arm 31 has a hole or slot through which pin 37 extends so that arm 31 can be moved about the pivot pin reciprocally toward and away from arm 33 along a plane passing through both of these handles, preferably through the center of their elongated axis. Integrally secured to the upper end of handle 31 is projection 22 which moves back and forth along same plane as does handle 31 when the handle is moved along at its hinge or pivot point about pin 37.

Referring also to FIG. 4, upper arm 18 has a recess 21 along one side of rear shoulder portion 20 for receiving projection 22. Projection 22 extends upwardly and is integral with arm 31 as is hinge pin 37. Thus, as handle 31 is reciprocally moved, projection 22 will move back and forth in slot 42 with hinge pin 37 pivoting in notch 47 cut into bridge portion 11 of stationary handle 33. Notch 47 is slightly restricted just below hinge pin 37 so that the pin will pass through the restriction and snap into place on assembly. On disassembly, arm 31 is urged downwardly with pin 37 snapping through the restriction and the notch. Upper arm 18 slidably engages stationary lower arm 16 along part line 41, so that with projection 22 received in recess 21, as handle 31 is reciprocated, it will cause concomitant (and opposite) reciprocation of arm 18.

Referring further to FIG. 1, at the opposite end of arms 16 and 18 are jaws 14 and 12 respectively. Jaw 14, the lower jaw, is stationary and an integral extension of arm 16. Upper jaw 12 is moved up and down in a reciprocal manner as arm 18 reciprocates. This jaw movement is achieved by a pivot member 46 received in a slot extending through jaw 14 and which pivot member is mounted on pivot pin 15 through jaw 14. The rear end of upper jaw 12 is firmly secured to pivot member 46 which pivot member is also pivotally connected to the end of arm 18 at pivot pin 17. Accordingly, as upper arm 18 is retracted or moved rearwardly, it pulls pivot member 46 rearwardly via pivot pin 17 which also causes the pivot member to pivot on pivot pin 15 and elevates jaw 12. This movement is in response to reciprocal movement of handle 31, and as previously explained causes projection 22 to move reciprocal arm 18 via recess 21 in which the projection is received. In other words, as the handles are opened, so are the jaws.

The desirable feature of the instrument is its ability to be partially and easily disassembled as illustrated in FIG. 4 by which upper and lower arms 18 and 16 are disengaged. Referring to FIG. 3, this is achieved by urging shoulder 20 of arm 18 to the right, which, because of the flexibility of elongated arm 18 allows recess 21 to be displaced from projection 22. Once the projection is free from the recess, arm 18 can be pulled upwardly as shown in FIG. 4 and the instrument cleaned. This is particularly important along part line 41 between the upper and lower arms which portion of the instrument is usually placed in the incision during the surgery. As convenient as is this ability to be partially disassembled and cleaned, there results a problem where the locking means is not provided. For example, when a right handed surgeon is utilizing the instrument, in a microlumbar discectomy procedure, with the jaws and arms of the instrument inserted into the incision, the upper arm may come to rest or be forced against cartilage or bone. As the surgeon twists the device by urging the rings and handles clockwise in an attempt to pull away, remove or free material clamped in the jaws, with pressure being exerted against upper arm 18 by bone against which it is forced, this causes the arm to be displaced and shoulder 20 to be moved disengaging projection 22 from recess 21. As this occurs, the device becomes disassembled, in substantially the same manner as it would intentionally by one for cleaning. When the device becomes disassembled during a surgical procedure, with such an interruption, at which point the instrument fails to operate, it is most undesirable.

According to the invention, this problem is obviated by incorporating a locking member or bar 26 pivotally secured on the side of the instrument opposite recess 21. Observing particularly FIGS. 2 and 3 there is shown locking member 26 secured on pivot pin 30 engaged in a stationary arm 33. Being so pivoted, locking member 26 can be moved upwardly to engage the side of shoulder 20 as illustrated thereby preventing it from being moved to the right (FIG. 3) when in such a locked position so that the instrument cannot be disassembled in that condition. During use, as retractable handle 31 is moved, with concomitant back and forth reciprocal movement of arm 18 and shoulder 20, bar 26 can also move back and forth along with the arm and shoulder hinging on pivot pin 30. Since the distance of movement or stroke is rather short, there will not be excessive wear on the side of shoulder 20 which contacts or abuts the inner surface of bar 26. A very rigid bar may even be offset slightly so as not normally lie against the shoulder surface unless the arm is moved toward the bar during the twisting previously referred to. Moreover, a pair of small projections or protuberances 28 and 29 may be used to properly center or position bar 26 in the locked position and prevent inadvertent slippage and unlocking of the bar during repeated movement of the reciprocal arm. However, other similar means for assisting in maintaining the bar in the locked position so that it will not inadvertently slip out during use of the instrument may be substituted.

When it is desired to unlock the instrument for cleaning, the operator simply will push or pull bar 26 over the small projections or protuberances, and pivot it about pivot pin 30 until the upper part or portion of the bar has cleared part line 40 separating handle 33 and shoulder 20. Moreover, when in the locked position shown, the portion of bar 26 contacting the surface of shoulder 20 will be sufficient to prevent the shoulder and arm from being displaced, at least to the extent of removing or disengaging projection 22 from recess 21. In other words, the device shown prevents inadvertent and accidental unlocking of the device during surgical procedure and yet allows for unlocking when it is desired to clean the instrument.

Referring to FIGS. 5 and 6, there is shown another embodiment regarding the jaws. According to the invention, upper jaw 12 is provided with a tooth 32 which projects downwardly from normal or existing part line 41 between the jaws. Lower jaw 14 is provided with a recess 34 which has a perimeter of substantially the identical size and shape of the perimeter of tooth 32 so that when the jaws are closed, the tooth is fully seated within the recess and the surfaces meet. Further, it is preferred that the surface of both the tooth and recess as well as the surface of the upper and lower jaws at the part line be sharpened so that they will cut into tissue when the jaws are forced in the closed position. The tooth and the recess also give an irregular surface for more firmly gripping tissue or other material desired to be removed in the incision utilizing the forceps. The specific size of the tooth is not so important as is the fact that preferably it extends slightly around the forward end or nose of the jaws of the forceps as shown. Other specific shapes of the tooth and recess to achieve this desired function are within the purview of the invention. Finally, for a micro-lumbar discectomy use, the forceps should have arm lengths sufficient so that the ends of the jaws are at least 12 cm and preferably about 13 cm from the opposite end of shoulder 20. This length will provide an instrument well suited even for deep areas in the procedure.

I claim:

1. In forceps having a stationary first handle and first arm integrally secured thereto, a movable second handle pivotally secured on said stationary handle, and having a projecting member thereon received in an open recess along one side of a reciprocally moveable second arm, said second arm slidably mounted on said first arm, whereby pivotal movement of said second handle reciprocates said second arm, and whereby said second arm is disengageable by lateral movement away from said projecting member, the improvement comprising a stop member secured on said stationary handle for engaging the side of said second arm opposite said recess and preventing said lateral movement and disengagement thereof.

2. The forceps of claim 1 including a pivotally moveable jaw secured at an end of said second arm and a stationary jaw secured at an end of said first arm.

3. The forceps of claim 2 wherein one of said jaws has a tooth along a forward surface thereof and the other jaw has a notch for receiving said tooth when the jaws are closed.

* * * * *